(12) United States Patent
Muller-White

(10) Patent No.: US 11,813,144 B1
(45) Date of Patent: Nov. 14, 2023

(54) MULTI-LAYER COMPRESSION WRAP SYSTEM FOR TREATING VENOUS ULCERS AND RELATED CONDITIONS

(71) Applicant: Sandra P. Muller-White, Cresco, PA (US)

(72) Inventor: Sandra P. Muller-White, Cresco, PA (US)

( * ) Notice: Subject to any disclaimer, the term of this patent is extended or adjusted under 35 U.S.C. 154(b) by 436 days.

(21) Appl. No.: 16/734,289

(22) Filed: Jan. 3, 2020

Related U.S. Application Data

(60) Provisional application No. 62/787,877, filed on Jan. 3, 2019.

(51) Int. Cl.
| | | |
|---|---|---|
| *A61F 13/00* | (2006.01) | |
| *A61K 33/30* | (2006.01) | |
| *A61K 33/26* | (2006.01) | |
| *A61F 13/08* | (2006.01) | |

(52) U.S. Cl.
CPC .......... *A61F 13/00063* (2013.01); *A61F 13/08* (2013.01); *A61K 33/26* (2013.01); *A61K 33/30* (2013.01); *A61F 2013/00119* (2013.01)

(58) Field of Classification Search
None
See application file for complete search history.

(56) References Cited

U.S. PATENT DOCUMENTS

| | | | | |
|---|---|---|---|---|
| 7,854,716 | B2* | 12/2010 | Schuren et al. ...... | A61F 13/069 602/75 |
| 2002/0099318 | A1* | 7/2002 | Suehr et al. .......... | A61F 13/08 602/76 |
| 2007/0299383 | A1* | 12/2007 | Murphy et al. ... | A61F 13/00991 602/46 |
| 2013/0085435 | A1* | 4/2013 | Murphy et al. ........ | A61K 47/42 424/443 |
| 2014/0052043 | A1* | 2/2014 | Steinlechner et al. .................... | A61F 13/00029 602/76 |
| 2015/0157524 | A1* | 6/2015 | Reid, Jr. et al. ....... | A61F 13/06 601/84 |
| 2019/0262188 | A1* | 8/2019 | Reid, Jr. ................ | A61H 1/006 |

OTHER PUBLICATIONS https://web.archive.org/web/20170626051909/https://www.smith-nephew.com/key-products/advanced-wound-management/profore/, Archived on Jun. 26, 2017, 3 Pages, Retrieved from Internet Archive Wayback Machine on Dec. 28, 2021 Smith+Nephew Medical Devices and Advanced Wound Care.
https://web.archive.org/web/20170627035812/https://www.shopwoundcare.com/p-dynarex-unna-boot-bandages.html, Archived on Jun. 27, 2017, 3 Pages, Retrieved from Internet Archive Wayback Machine on Dec. 28, 2021 Shop Wound Care Compression Bandages.
https://web.archive.org/web/20181126073956/http://www.urgomedical.com/wp-content/uploads/urgok4.pdf, Archived on Nov. 26, 2018, 2 Pages, Retrieved from Internet Archive Wayback Machine on Dec. 28, 2021 UrgoK4/K-Four.
Moffatt, Four-layer bandaging: from concept to Practice Part 2: Application of the four-layer system, Mar. 2005, World Wide Wounds, pages 1-8. (Year: 2005).*

* cited by examiner

*Primary Examiner* — Kim M Lewis
(74) *Attorney, Agent, or Firm* — Wilkinson Law Office; Clinton H. Wilkinson

(57) ABSTRACT

A multi-layer compression bandage system (the "Sandy Boot") for treating patients having chronic venous insufficiencies and related conditions, including a first skin-contacting layer applied as a wet paste roll over the treated area, which bandage system is less prone to forming wrinkles, conforms well to the circumference of any shaped leg, adheres well to moist or dry skin due to its pliability, and resists slipping or rolling down the leg better than traditional bandage systems, thereby enhancing wound healing.

1 Claim, 1 Drawing Sheet

MULTI-LAYER COMPRESSION WRAP SYSTEM FOR TREATING VENOUS ULCERS AND RELATED CONDITIONS

CROSS REFERENCE TO RELATED APPLICATION

This application claims the benefit of U.S. Provisional Pat. Application Ser. No. 62/787,877 filed on Jan. 3, 2019, the entirety of which is now incorporated herein by reference.

FIELD OF THE INVENTION

The present invention relates to systems and methods for providing compression of venous tissue in the extremities to enable improved blood movement, and more particularly to compression bandage systems and methods for use in the treatment and management of chronic venous insufficiencies, venous ulcers, and related conditions.

BACKGROUND OF THE INVENTION

There are a large number of different compression therapies available for the treatment of wounds, some of which have been found to be more effective than others in treating particular conditions. Medical compression therapy (CT) is commonly used to treat and manage chronic venous insufficiency (CVI) (venous valvular reflux), which occurs mainly in the lower calf and ankle of the leg and is the most common cause of lower extremity ulceration, as well as other chronic venous related conditions. Compression therapy is also widely used to treat conditions such as thrombosis, edema, burns, and sprains. Topical compression therapy is known to increase venous flow, which enhances healing, and involves the selective use of various bandages, wraps, sleeves, and stockings / hosiery, as well as other compression therapy devices such as devices having one or more air cells that are filled with a gas by an electric or manual pneumatic pump.

Compression bandages are categorized according to the stiffness. Short-stretch bandages are inelastic and have a higher stiffness factor, while long-stretch bandages are more elastic and have a lesser stiffness factor. Inelastic systems have a low resting pressure, such that a low amount of pressure or compression is applied when a patient is at rest, and a high working pressure, wherein a high pressure is asserted against the calf muscles as they contract during work activities such as walking, which helps push blood upwards out of the legs to the heart. Elastic systems, in contrast, have both a high resting pressure and a high working pressure. Inelastic systems are considered safer and more appropriate for venous insufficiency complicated by arterial disease, while elastic systems are generally not considered safe for use on patients with coexisting arterial disease.

One compression bandage system commonly used today on patients with venous insufficiency is a multi-layer wrap system. This bandage system is available under the trade designations "Profore" by Smith & Nephew, Inc. and "K4" from Urgo Medical. The inner layer is typically a cotton or orthopaedic wool or natural wadding roll which is applied somewhat loosely to the circumference of the lower leg. This layer provides cushioning and padding, including to bony prominences, redistributes and evens the pressure applied by the bandage system around the lower leg, and absorbs exudate. The next layer is a noncompressive light support bandage that adds absorbency and smooths the first layer prior to application of the outer layers. The third layer is the first layer of elastic compression and is a light compression bandage, which is applied in a figure eight pattern and is able to provide and maintain up to about 20 mmHg at the ankle and up to about 15 mmHg at the calf. The outer layer is a selfadherent (cohesive) flexible bandage which provides a second layer of compression up to about another 25 mmHg at the ankle. Compression is therefore built up gradually due to the use of two compression layers.

A disadvantage of such multi-layer wrap system is that the cotton roll or padding layer does not grip well to the skin, and with repeated patient ambulation or day to day activity tends to settle or slip, form wrinkles, and roll down the leg in only a fairly short time after being applied. This is particularly true with respect to certain patients having lower leg dimensions outside of a normal range, including those with large legs in general as well those having an unusually small ankle circumference and/or an unusually large calf circumference. For example, some patients with advanced chronic venous insufficiency develop lipodermatosclerosis (LDS), a symptom of which is skin induration or thickening either before or surrounding leg ulcers, and that the lower leg takes on an inverted champagne bottle shape or appearance. Such unusual dimensions make it easier for the multi-layer bandage to slide down due to gravity and movement even after the outer compression layers are applied to complete the four layers. An additional layer of cotton padding is sometimes added to the narrowest part of the leg, but this has only a limited effectiveness in reducing sliding or rolling of the bandage, particularly with more mobile patients.

Settling or slipping of a compression bandage can greatly reduce the effectiveness of the bandage system, since the desired pressure applied by the bandage is not maintained, or becomes uneven. In addition, the forming of wrinkles in the bandage can result in discomfort to the patient. Significant slipping down the leg may also require the dressing to be removed so that it does not rub again the skin and possibly cause new wounds, and in some cases the wound undesirably may become exposed. On the other hand, as indicated above long stretch or elastic bandages which are less prone to slipping are not appropriate for use with chronic venous insufficiency.

BRIEF SUMMARY OF THE INVENTION

A multi-layer compression bandage system for treating patients having venous leg ulcers and related conditions of the lower leg that is less prone to forming wrinkles and slipping down the leg than current bandage systems. Advantageously, the present bandage system is particularly beneficial to patients who have difficulty maintaining a traditional Profore or K4 compression bandage, such as patients having larger than normal legs or unusually shaped lower legs with a disproportionately large diameter calf and small ankle.

The multi-layer compression bandage system of the present invention includes four separate layers of latex-free wraps in addition to in some embodiments a cotton tubular outer roll that creates a neat finish to the system, and provides compression for up to 7 days, with a 30 - 40 mm Hg compression range. The first layer is provided as a wet paste roll, which when applied as the first layer will grip to the skin and conforms well to the circumference of any shaped leg, therefore, adhering to both moist and dry skin due to its pliability. Utilization of a wet paste inner layer therefore greatly reduces the possibility of the wrap slipping or rolling and causing trauma to the leg.

In some embodiments, the first layer is an inelastic bandage usually made of cotton or orthopaedic wool which has been impregnated with a paste-like mixture of zinc oxide and/or calamine. In a preferred embodiment, the inner conforming paste layer is an Unna boot bandage. In an embodiment, the second layer primarily absorbs exudate or drainage, while the third and fourth layers together provide a graduated compression. The combination of the conforming paste bandage inner layer with a conforming bandage second, the light compression bandage third layer, and a self-cohesive bandage fourth layer, a better, more even compression is provided as compared to prior art multi-layer bandage systems.

In some embodiments, the present system is a compression bandage system for treating leg ulcers comprising: a skin contact layer formed of an elongated conforming paste bandage which is impregnated with a zinc oxide composition; a second layer comprising an elongated conforming bandage applied separately on the skin contact layer, a third layer comprising an elongated light compression bandage applied separately on the second layer, and an outer layer comprising a self-cohesive elastic bandage applied separately on the third layer.

In some embodiments, the present system is a multi-layer compression bandage system (the "Sandy Boot") which consists of four separate layers of latex-free wraps in addition to a cotton tubular outer roll that creates a neat finish to the system, and provides compression for up to 7 days, with a 30 - 40 mm Hg compression range. The "Sandy Boot" greatly reduces the possibility of the wrap slipping or rolling and causing trauma to the leg. In particular, the first layer is provided as a paste roll, which when applied as the first layer will grip to the skin and conforms well to the circumference of any shaped leg, therefore, adhering to both moist and dry skin due to its pliability.

Further areas of applicability of the present invention will become apparent from the detailed description provided hereinafter.

BRIEF DESCRIPTION OF THE DRAWINGS

The present invention will become more readily understood from the detailed description in conjunction with the accompanying drawings, wherein like reference numerals designate like structural elements, and wherein.

DETAILED DESCRIPTION OF THE INVENTION

Reference will now be made in detail to representative embodiments of the present invention as illustrated in the accompanying drawings. The following descriptions are not intended to be understood in a limiting sense, but to be an example of the invention presented solely for illustration thereof, and by reference to which in connection with the following description and the accompanying drawings one skilled in the art may be advised of the advantages and construction of the invention.

Four-layer compression bandage systems are commonly used in the treatment of venous ulceration. In conventional four-layer systems, the first layer is a cotton or orthopaedic wool padding layer which is supposed to protect areas at risk of high pressure, such as the foot and ankle as well as any bony prominences. However, the padding layer is a dry thick padding which when applied on moist to dry skin does not adhere well to the skin, so that with ambulation and day to day activity of the patient the bandage will tend to roll down the leg. The present inventor therefore has developed a multi-layer compression bandage system that does not have the same tendency to slide, wrinkle or roll, wherein the dry thick padding inner layer is replaced with a wet paste bandage.

Figure 1:
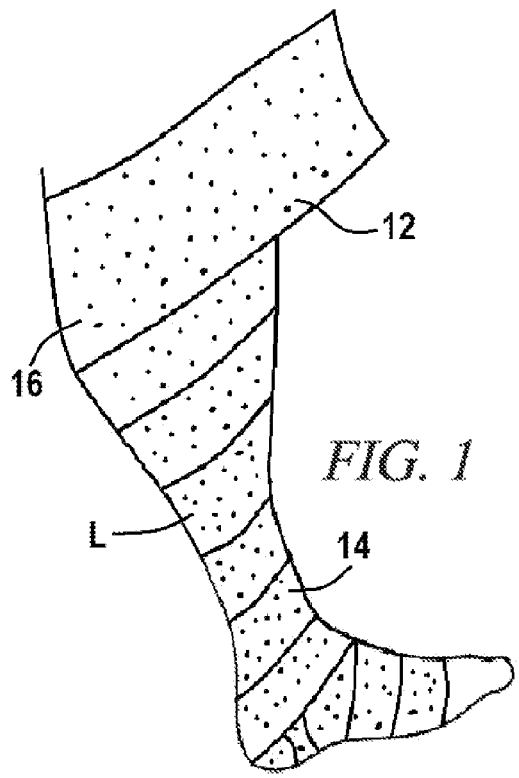
FIG. 1 is a depiction from the side showing a first layer of the wound bandage system of an embodiment of the present invention applied on a lower leg.

FIG. 1 illustrates a lower leg L having a conforming paste bandage 12 applied to the leg as the inner layer of the compression bandage system of the present invention. Leg L is intended to illustrate a lower leg having an unusual shape, in that the ankle area 14 has a smaller than normal circumference, while the calf area 16 has a somewhat larger than normal circumference, which is symptomatic of advanced chronic venous insufficiency. The conforming paste bandage 12 is a compression bandage made of a natural material such as cotton or an orthopaedic wool gauze, and is used to absorb small to moderate amounts of drainage or exudate. As shown in FIG. 1, the bandage 12 is applied over the foot, ankle, and calf area in a spiral fashion, starting about one-half (½) inch below the toes and ending at about 1 inch below the knee (at the tibial tubercle). The foot should be at an angle of 90 degrees with respect to the leg when the bandage 12 is applied so that it will not bunch up or become loose after application. The bandage 12 should be overlapped by about one-half the width, and should be wrapped with a light tension so it remains in place, but not so tight that the bandage 12 is uncomfortable when the patient walks or moves around. Importantly, the paste bandage 12 should be smoothed out as much as possible so there are no wrinkles. Any remaining paste bandage should not be wrapped going back down the lower leg.

A suitable conforming paste bandage for use as the innermost bandage layer 12 of the compression bandage system of the present invention is the "Unna" boot, invented by German dermatologist Dr. Paul Gerson Unna. The Unna boot consists of an inelastic bandage usually made of a woven cloth such as cotton or orthopaedic wool gauze which has been impregnated with a medicated paste-like mixture of zinc oxide and/or calamine which is on a glycerin and/or gelatin support, and in some embodiments may contain other ingredients such as methylparaben, propylparaben, acacia, castor oil, white petrolatum, ictamol, and others. In an embodiment, the bandage 12 is impregnated with a zinc oxide composition containing between about 10%-20% by weight zinc oxide, and in another embodiment up to 10% by weight of calamine. The Unna boot bandage is a low compression bandage which provides between 20-30 mm-Hg in pressure, and the paste maintains a moist environment that encourages healing and eases skin irritation, while still remaining sufficiently flexible so that it conforms well to the leg.

The Unna boot bandage can absorb light to moderate amounts of drainage, and works with the contraction of the calf muscle to force one-way bicuspid valves in the veins open in order to move fluids. Thus, this bandage is primarily indicated for patients who are ambulatory, and since it only provides a low compression when the patient is at rest, it is not recommended for sedentary or wheelchair bound patients. The Unna boot is also not appropriate for use on patients with arterial or mixed ulcers, swelling, erythema, or extensive inflammation in the ulceration area, or on patients with uncontrolled diabetes mellitus. An antibiotic cream, antiseptic, or dressing may be applied to the wound prior to the paste conforming bandage 12.

Figure 2:
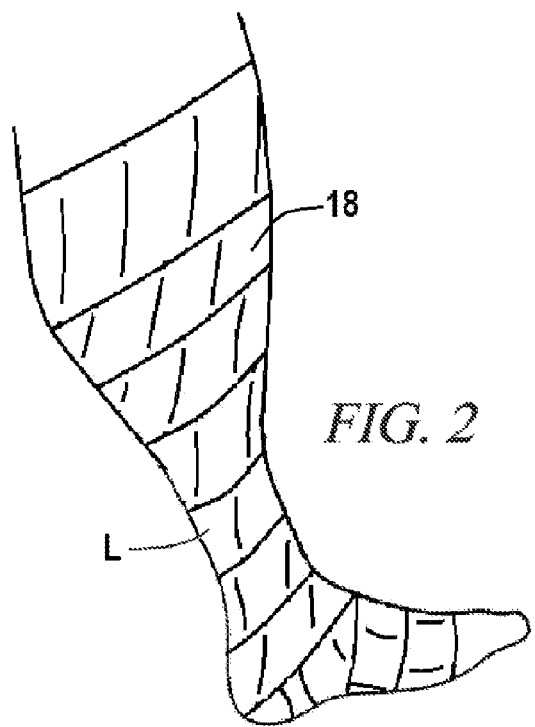
FIG. 2 is a depiction from the side showing a second layer of the wound bandage system of an embodiment of the present invention applied on a lower leg.

Referring now to FIG. 2, once the conforming paste bandage 12 has been applied as shown in FIG. 1 and is secured, a conforming bandage 18 is applied as a secondary dressing over the conforming paste bandage 12. The conforming bandage 18 will absorb excessive drainage if needed. In some embodiments, the conforming bandage 18 is a 100% cotton 2-ply woven bandage which provides a light stretch that enables the bandage 18 to conform to body contours while providing only minimal or no actual compression. In an embodiment, a suitable conforming bandage 18 is the Profore #2 light conformable bandage manufactured by Smith & Nephew, Inc. In another embodiment, the conforming bandage 18 may be a knitted stretch gauze made of a synthetic material.

The second conforming bandage 18 layer should be wrapped in the same manner as the first layer. More particularly, the conforming bandage 18 may be a crepe bandage which is applied over the foot, ankle, and calf area in a spiral fashion, starting about one-half inch below the toes and ending at about 1 inch below the knee (at the tibial tubercle). The foot should be at an angle of 90 degrees with respect to the leg when the conforming bandage 18 is applied, and the bandage 18 should be overlapped by about by one-half the width. The second layer conforming bandage 18 is then secured with a tape. In some embodiments, if additional protection is needed, a padding may be placed over portions of foot and ankle after the inner conforming paste bandage 12, but before the second layer conforming bandage 18 is applied. The cotton padding will adhere to the outer surface of the wet paste bandage 12 and therefore resists slipping or wrinkling. This may also add comfort to the bandage system for some patients, and also absorb additional drainage.

Figure 3:
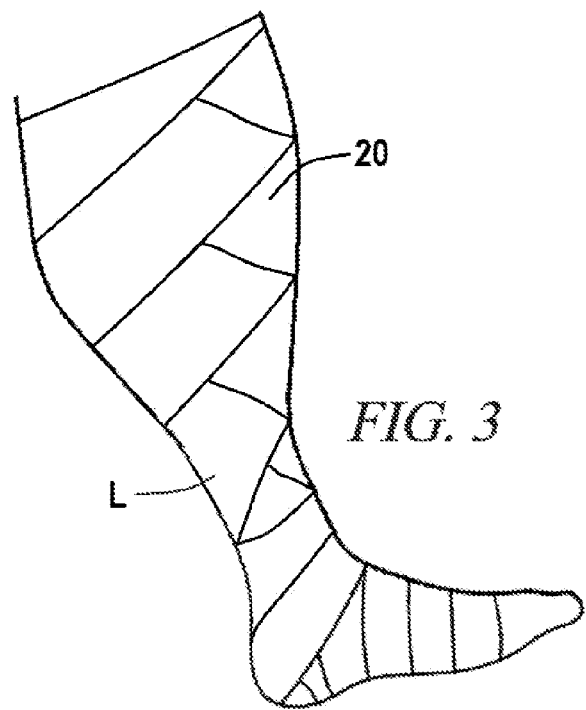
FIG. 3 is a depiction from the side showing a third layer of the wound bandage system of an embodiment of the present invention applied on a lower leg.

Referring now to FIG. 3, a third layer, which is formed of a light compression bandage 20, is then applied over the first layer paste bandage 12 and second layer conforming bandage 18. Starting at the foot and from the foot to the ankle, light compression bandage 20 is wrapped in the same spiral technique used in applying the paste bandage 12 and conforming bandage 18. Starting at the ankle, however, as shown in FIG. 3 the light compression bandage 20 is then applied using a criss cross or figure eight technique from the ankle up to about 1 inch below the knee. In an embodiment, a suitable light compression bandage 20 is the Profore light compression bandage manufactured by Smith & Nephew, Inc. In some embodiments, when wrapping, black lines on the bandage are used as a guide for obtaining correct 30/40 mmHg pressure. The black lines must produce an "X" design to be at the desired 50% relaxed stretch length. The light compression bandage 20 is then secured with a tape.

Figure 4:
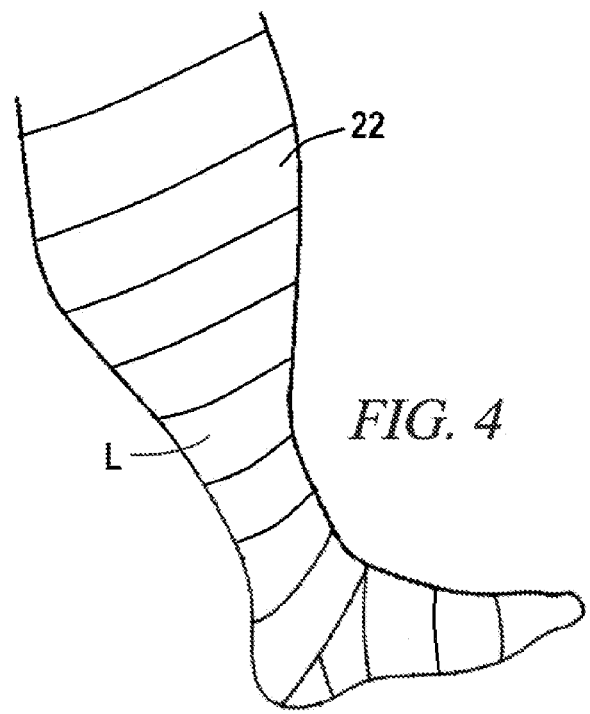
FIG. 4 is a depiction from the side of a fourth layer of the wound bandage system of an embodiment of the present invention applied on a lower leg.

Referring now to FIG. 4, a fourth layer, which is formed of a flexible self-cohesive bandage 22, is applied over the light compression bandage 20. The self-cohesive bandage 22 is applied in the same spiral manner as the paste bandage 12 and conforming bandage 18 starting at the base of the toes and up to just below the knee. Each layer of the self-cohesive bandage 22 is overlapped by one-half the width. This self-cohesive bandage layer 22 must be stretched to a relaxed 50% while wrapping around the leg on a full turn. The self-cohesive bandage layer will adhere to itself, although the cohesiveness is increased by molding and squeezing the bandaged leg. In an embodiment a suitable self-cohesive bandage 22 for use in accordance with the present invention is the Profore #4 flexible cohesive bandage manufactured by Smith & Nephew, Inc.

Lastly, the bandage layers may be enclosed in a tubular elastic dressing retainer, not shown, to protect the "Sandy Boot" compression system. This step is optional. In an embodiment, a suitable dressing retainer is the size 7 tubular elastic dressing retainer manufactured by McKesson.

Unlike prior art compression bandage systems, in which the initial or skin contacting layer is a padding layer, in the present inventor's bandage system the skin contacting layer is wet paste bandage impregnated with zinc oxide which makes it wet and pasty. A principal advantage of the present invention over prior art compression bandage systems is that when first applied the wet paste compression bandage is flexible and therefore conforms well to any shaped leg, including legs having an unusually large calf or unusually small ankle. The wet paste bandage will dry slowly over time, but as it dries, it will remain soft to the touch, and provides better comfort and control than prior art compression bandage systems. It may stiffen slightly but will not harden like a cast, and resists slipping and wrinkling over time.

The present compression bandage system is advantageous over the conventional Unna boot in that it adds two additional compression layers, and is advantageous over existing four-layer bandage systems used for venous insufficiency in that the wet paste bandage 12 is a compression bandage which therefore adds a third compression layer to the bandage system that resists slipping or wrinkling. The Unna boot or paste roll is specifically made to absorb light-to-moderate drainage, and wicks away drainage from the skin, while at the same time, keeps open ulcers moist for wound healing. In contrast, use of a cotton roll first layer will tend to desiccate ulcers if applied directly to the open wound which is not conducive for wound healing. As a result, better control over the amount of compression is available, and the compression is maintained at a desired uniform level more easily than with prior art compression bandages. In addition, with use of an initial cotton layer, a dressing must be first applied to an open wound. With the Unna boot, although a dressing may be applied, it may also go directly on the open wound. The Unna boot protects the open ulcer. It will not stick to an open ulcer like the cotton roll will. The cotton roll does not protect open ulcers, but rather is made to protect boney areas. Providing an inner layer that is medicated is also therefore extremely advantageous in aiding in wound healing.

Contra indications: The Ankle Brachial Pressure Index (ABI) which is a test for the presence of peripheral artery disease (PAD), or more particularly narrowed arteries that reduce blood flow, usually in the legs, must be performed prior to application of the "Sandy Boot" of the present invention. An ABI of less than 0.9 indicates the presence of arterial disease. If arterial id is present, DO NOT apply the "Sandy Boot". DO NOT apply the Sandy Boot if ABI is greater than 1.3 which is considered suggestive of non-compressible vessels.

While the present invention has been described at some length and with some particularly with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

What is claimed is:

1. A method for applying a compression bandage system intended particularly for treating patients with lower leg ulcers and related chronic venous conditions to a lower leg having a prominent calf and narrow ankle comprising: providing a plurality of bandage layers including a first skin contacting layer comprising an elongated conforming paste bandage impregnated with a zinc oxide composition, a second layer comprising an elongated conforming bandage configured to be applied separately on and over the skin contacting layer, a third layer comprising an elongated light compression bandage configured to be applied separately on and over the second layer, and an outer layer comprising a self-cohesive elastic bandage configured to be applied separately on and over the third layer; applying the skin contacting layer over and around the lower leg in a spiral, partially overlapping fashion; applying the second layer over and around the skin contacting layer also in a partially overlapping manner; applying the third layer over and around the second layer in a criss cross or figure 8 pattern and with a desired stretch length; applying the fourth layer over and around the third layer in a partially overlapping manner and with a desired stretch length; and allowing the first layer to dry; wherein the first layer conforms to the shape of the patient's lower leg when applied around the lower leg, and when dry has a stiffness which reduces sliding or rolling of the compression bandage system down the lower leg.

* * * * *